United States Patent
Wu et al.

(10) Patent No.: US 12,183,443 B2
(45) Date of Patent: *Dec. 31, 2024

(54) SMART CONTROL SYSTEM

(71) Applicant: PixArt Imaging Inc., Hsin-Chu County (TW)

(72) Inventors: Sung-Han Wu, Hsin-Chu County (TW); Yi-Hsien Ko, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 0 days.

This patent is subject to a terminal disclaimer.

(21) Appl. No.: 18/484,454

(22) Filed: Oct. 11, 2023

(65) Prior Publication Data

US 2024/0038353 A1 Feb. 1, 2024

Related U.S. Application Data

(63) Continuation of application No. 16/993,472, filed on Aug. 14, 2020, now Pat. No. 11,817,194, which is a continuation-in-part of application No. 16/683,946, filed on Nov. 14, 2019, now Pat. No. 11,381,418, and a continuation-in-part of application No. 16/398,778, filed on Apr. 30, 2019, now Pat. No. 11,137,770.

(51) Int. Cl.
| | | |
|---|---|---|
| *G16H 20/10* | (2018.01) | |
| *G06F 16/955* | (2019.01) | |
| *G16Y 10/60* | (2020.01) | |
| *G16Y 10/80* | (2020.01) | |
| *G16Y 20/10* | (2020.01) | |
| *G16Y 20/40* | (2020.01) | |
| *G16Y 40/10* | (2020.01) | |

(52) U.S. Cl.
CPC ......... *G16H 20/10* (2018.01); *G06F 16/9554* (2019.01); *G16Y 10/60* (2020.01); *G16Y 10/80* (2020.01); *G16Y 20/10* (2020.01); *G16Y 20/40* (2020.01); *G16Y 40/10* (2020.01)

(58) Field of Classification Search
CPC .... G06F 16/9554; G16H 20/10; G16Y 10/60; G16Y 10/80; G16Y 20/10; G16Y 20/40; G16Y 40/10
See application file for complete search history.

(56) References Cited

U.S. PATENT DOCUMENTS

| | | | | |
|---|---|---|---|---|
| 7,269,480 B2 * | 9/2007 | Hashimoto | ............ | G06N 3/004 700/262 |
| 8,063,872 B2 * | 11/2011 | Forstall | ................. | G06F 1/3203 713/323 |

(Continued)

FOREIGN PATENT DOCUMENTS

| | | |
|---|---|---|
| CN | 103635862 A | 3/2014 |
| CN | 104898440 A | 9/2015 |

(Continued)

*Primary Examiner* — Babar Sarwar
(74) *Attorney, Agent, or Firm* — HAUPTMAN HAM, LLP

(57) ABSTRACT

There is provided a smart control system including a host, at least one sensor and an informing device. The host identifies the activity of a specific member according to the detection result of the at least one sensor, and informs the specific member to take medicine on time or avoid eating specific ingredients using the informing device.

20 Claims, 4 Drawing Sheets

(56) References Cited

U.S. PATENT DOCUMENTS

| | | | |
|---|---|---|---|
| 8,577,392 B1* | 11/2013 | Pai | H04W 4/029 455/456.2 |
| 8,810,388 B2 | 8/2014 | Jacobs et al. | |
| 8,918,121 B2* | 12/2014 | LeBeau | H04M 1/72403 455/457 |
| 9,685,059 B2* | 6/2017 | Wang | G08B 17/12 |
| 9,852,261 B1* | 12/2017 | Havard | G16H 70/40 |
| 10,462,611 B1 | 10/2019 | Klinkner et al. | |
| 10,552,575 B1* | 2/2020 | Mohebbi | G06F 18/22 |
| 10,599,174 B2* | 3/2020 | Baker | H05B 47/1965 |
| 10,687,193 B2* | 6/2020 | Booth | G06F 1/3287 |
| 10,802,459 B2* | 10/2020 | Frenz | F24F 11/00 |
| 11,019,149 B2* | 5/2021 | Kim | H04L 12/2834 |
| 11,094,124 B1* | 8/2021 | Schweinfurth | G16H 40/20 |
| 11,137,770 B2* | 10/2021 | Ko | G05D 1/247 |
| 11,205,503 B2* | 12/2021 | Rothschild | G16H 20/10 |
| 11,539,526 B2* | 12/2022 | Channa | H04L 63/123 |
| 2003/0051146 A1* | 3/2003 | Ebina | H04L 63/0428 380/278 |
| 2005/0197989 A1* | 9/2005 | Hori | H04L 12/2829 706/47 |
| 2006/0293810 A1* | 12/2006 | Nakamoto | G05D 1/0274 701/28 |
| 2007/0132575 A1* | 6/2007 | Ellul | G08B 17/00 340/584 |
| 2007/0192910 A1* | 8/2007 | Vu | H04N 7/142 901/1 |
| 2009/0243852 A1* | 10/2009 | Haupt | G06F 3/04845 709/224 |
| 2010/0094460 A1* | 4/2010 | Choi | G05D 1/0274 700/251 |
| 2010/0256812 A1* | 10/2010 | Tsusaka | B25J 5/007 700/254 |
| 2010/0312578 A1* | 12/2010 | Hardaway | G06Q 30/0207 705/14.1 |
| 2011/0082867 A1* | 4/2011 | Bruns | G16B 20/00 707/736 |
| 2011/0119073 A1* | 5/2011 | Hanina | G06F 16/24573 705/2 |
| 2012/0005222 A1* | 1/2012 | Bhagwan | G06F 16/5838 707/769 |
| 2012/0083669 A1* | 4/2012 | Abujbara | G16H 20/60 600/300 |
| 2012/0197439 A1* | 8/2012 | Wang | B25J 9/1664 901/1 |
| 2012/0213443 A1* | 8/2012 | Shin | G05D 1/0274 901/1 |
| 2012/0316680 A1* | 12/2012 | Olivier, III | G05D 1/0246 901/1 |
| 2013/0073094 A1* | 3/2013 | Knapton | G05B 13/02 700/278 |
| 2013/0321123 A1 | 12/2013 | Wan | |
| 2014/0074496 A1 | 3/2014 | Tsai | |
| 2015/0118630 A1* | 4/2015 | Ewell | A47J 31/525 432/32 |
| 2015/0204561 A1* | 7/2015 | Sadwick | F24F 11/33 236/1 C |
| 2015/0283036 A1* | 10/2015 | Aggarwal | A61J 7/0436 206/534 |
| 2016/0005229 A1* | 1/2016 | Lee | G06T 11/60 345/419 |
| 2016/0189365 A1* | 6/2016 | Lee | G06V 20/10 382/103 |
| 2016/0240060 A1* | 8/2016 | Wang | H04L 12/6418 |
| 2016/0323433 A1* | 11/2016 | Anderson | H04W 48/04 |
| 2017/0169185 A1* | 6/2017 | Weng | G16H 40/67 |
| 2017/0192435 A1 | 7/2017 | Bakhishev et al. | |
| 2017/0300665 A1* | 10/2017 | Wei | G16H 20/10 |
| 2018/0121629 A1* | 5/2018 | Dyer | G06Q 40/08 |
| 2019/0013960 A1* | 1/2019 | Sadwick | H05B 47/19 |
| 2019/0188473 A1* | 6/2019 | Witt | G06V 20/64 |
| 2019/0204844 A1* | 7/2019 | Lau | G05D 1/0274 |
| 2019/0278441 A1* | 9/2019 | Haupt | G01W 1/10 |
| 2019/0332114 A1* | 10/2019 | Moroniti | G01C 21/3807 |
| 2019/0380662 A1* | 12/2019 | Kwan | G16H 20/13 |
| 2020/0070355 A1* | 3/2020 | Neumann | B25J 13/084 |
| 2020/0085105 A1* | 3/2020 | Barbaric | G06F 16/9035 |
| 2020/0085694 A1* | 3/2020 | Patel | G08B 21/24 |
| 2020/0175864 A1 | 6/2020 | Solmaz et al. | |
| 2020/0296585 A1* | 9/2020 | Bolotin | H04W 12/06 |
| 2020/0345588 A1* | 11/2020 | Merrell | A61M 15/009 |
| 2020/0348688 A1* | 11/2020 | Ko | G05D 1/0276 |
| 2021/0014064 A1* | 1/2021 | Channa | H04L 63/0876 |
| 2022/0257118 A1* | 8/2022 | Soni | A61B 5/4839 |
| 2024/0171293 A1 | 5/2024 | Bakhishev et al. | |

FOREIGN PATENT DOCUMENTS

| | | |
|---|---|---|
| CN | 105553796 A | 5/2016 |
| CN | 105844452 | 8/2016 |
| CN | 107861451 A | 3/2018 |
| CN | 108022077 | 5/2018 |
| CN | 108052014 A | 5/2018 |
| TW | 201901538 | 1/2019 |

* cited by examiner

| | state indication | switch control |
|---|---|---|
| member1 | 1 (home) | 1st member enter or leave, turning on/off 1st switch set |
| member2 | 0 (absent) | 2nd member enter or leave, turning on/off 2nd switch set |
| member3 | 1 (home) | 3rd member enter or leave, turning on/off 3rd switch set |
| . . . | . . . | stay member combination I, 1st switch combination |
| | | stay member combination II, 2nd switch combination . . |

FIG. 2

SMART CONTROL SYSTEM

RELATED APPLICATIONS

The present application is a continuation application of U.S. patent application Ser. No. 16/993,472 filed on Aug. 14, 2020, which is a continuation-in-part application of U.S. patent application Ser. No. 16/398,778 filed on Apr. 30, 2019 and is also a continuation-in-part application of U.S. patent application Ser. No. 16/683,946 filed on Nov. 14, 2019, the disclosures of which are hereby incorporated by reference herein in their entirety.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

BACKGROUND

1. Field of the Disclosure

This disclosure generally relates to a smart home control system and, more particularly, to a smart home control system that turns on and off multiple electronic devices or informs a specific family member to execute recorded agenda according to the entering and leaving of family members.

2. Description of the Related Art

The smart home is one part of developing a smart city. However, in addition to basic controls of home appliances and lamps, it is also an important issue in a smart home to perform controls corresponding to different family members because different family members generally have different requirements. Besides, when multiple different events are detected, if the system can identify the relationship between the multiple different events and actively give a suggestion to deal with the related events together, performance of the smart home can be further improved, thereby increasing the life convenience.

Accordingly, the present disclosure provides a smart home control system that performs the indoor control or message prompting according to the ID of a member who enters or leaves the house to allow the smart home to be more user-friendly.

SUMMARY

The present disclosure provides a smart home control system that turns on and off control switches according to the member ID of staying members and/or absent members to improve the security and convenience of life.

The present disclosure further provides a smart home control system that identifies the relationship between recorded agenda and current events, and informs a specific member to execute the agenda related to the current event to improve the user experience of the smart home.

The present disclosure provides a smart control system including a memory, at least one sensor and a host. The memory is configured to record multiple agenda each being recorded using an item code comprising a member bit indicating a member ID associated with an agendum, a category bit indicating a type of the agendum and a temporal bit indicating an interval of the agendum. The at least one sensor includes an image sensor. The host is coupled to the memory and the at least one sensor, and configured to give a new item code and a pill feature of a taking medicine agendum to be added in the memory when one of the at least one sensor detects the taking medicine agendum, give an event code, which comprises bits corresponding to item bits of the item code, of a predetermined time event to be recorded in the memory, compare the event code of the predetermined time event with recorded multiple item codes by calculating similarity therebetween using software embedded in the memory when the predetermined time event occurs to remind the taking medicine agendum, and recognize, according to an image frame captured by the image sensor, whether pills matching the pill feature of the taking medicine agendum are mistakenly taken to give corresponding warning.

The present disclosure further provides a smart control system including a memory, at least one sensor and a host. The memory is configured to record multiple agenda each being recorded using an item code comprising a member bit indicating a member ID associated with an agendum, a category bit indicating a type of the agendum and a temporal bit indicating an interval of the agendum. The at least one sensor includes an image sensor. The host is coupled to the memory and the at least one sensor, and configured to give a new item code of a forbidden agendum, recorded with an image code, to be added in the memory when one of the at least one sensor detects the forbidden agendum, give an event code, which comprises bits corresponding to item bits of the item code, of a food event when the food event is recognized using one of the at least one sensor, and compare the event code of the food event with recorded multiple item codes by calculating similarity therebetween using software embedded in the memory to remind the forbidden agendum in the storage location recognized according to an image frame captured by the image sensor, having a captured image code to be compared with the recorded image code, to prevent forbidden ingredients from being eaten.

The present disclosure further provides a smart control system including a memory, an image sensor and a host. The memory is configured to record multiple forbidden agenda each being recorded using an item code comprising a member bit indicating a member ID associated with an agendum and a category bit indicating a type of the agendum, wherein the category bit indicates forbidden ingredients recorded using image codes in the memory. The image sensor is configured to capture an image frame. The host is coupled to the memory and the image sensor, and configured to give an event code, which comprises bits corresponding to item bits of the item code, of a food event when the food event is recognized according to the image frame, and compare the event code, recognized according to the image frame captured by the image sensor, of the food event with multiple item codes of the multiple forbidden agenda by calculating similarity therebetween using software embedded in the memory, and give a prompt when the event code matches one of the multiple item codes to prevent the forbidden ingredients from being eaten.

In the present disclosure, the agenda include items triggered or not triggered by a member. For example, detecting an object storage at home by a sensor is considered not being triggered by a member, accessing content in an electronic calendar may be considered being triggered by a member, and analyzing the conversation of family members is considered being triggered by a member. The agenda include, for example, at least one of purchasing objects, people contact, paying bills, carrying objects, proceeding positions or the like.

In the present disclosure, the current event is generally triggered by a family member, e.g., including family member exiting and family member having a phone call.

BRIEF DESCRIPTION OF THE DRAWINGS

Other objects, advantages, and novel features of the present disclosure will become more apparent from the following detailed description when taken in conjunction with the accompanying drawings.

FIG. 2 is a schematic diagram of correspondence relationship in a smart home control system according to a first embodiment of the present disclosure.

DETAILED DESCRIPTION OF THE EMBODIMENT

It should be noted that, wherever possible, the same reference numbers will be used throughout the drawings to refer to the same or like parts.

The smart home control system of the present disclosure is used to identify the entering and leaving of a family member according to detection results of at least one sensor, and to control the on/off or strength of a plurality of controlled devices or to inform a specific family member to execute recorded agenda by an informing device according to a ID of the family member who is identified to enter or leave the house.

Figure 1:
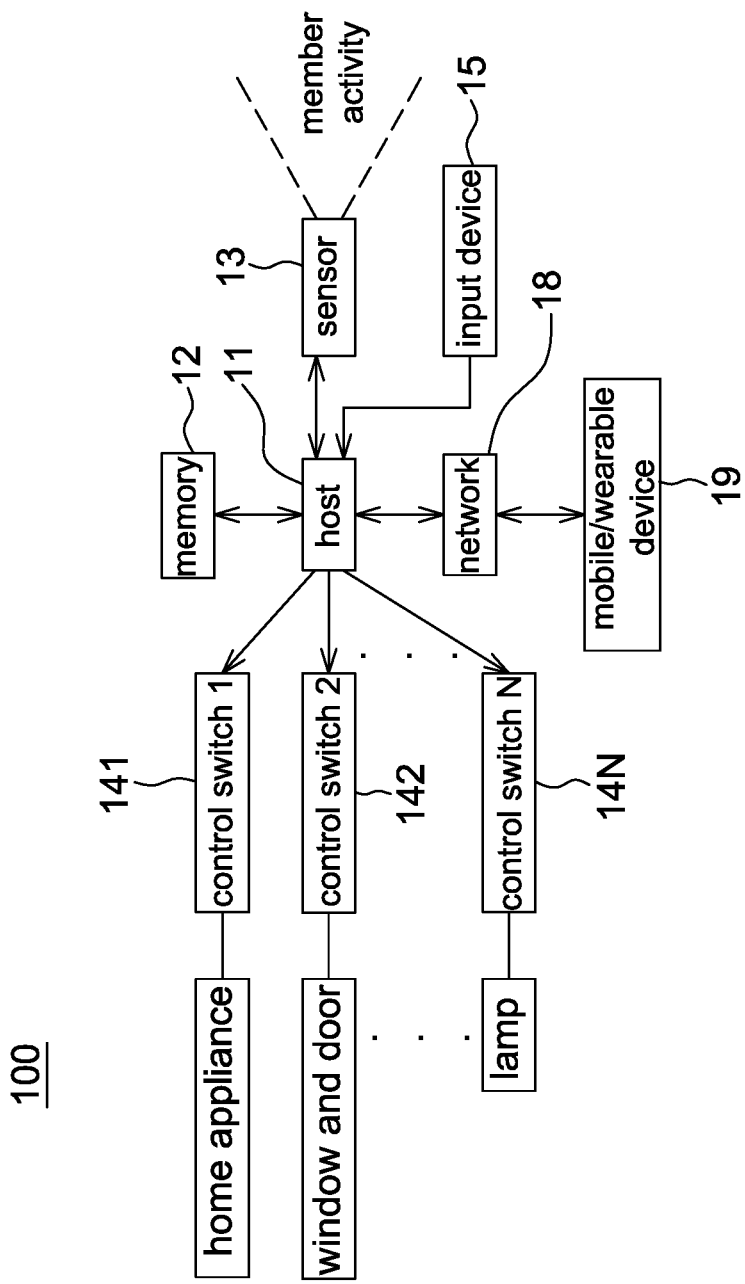
FIG. 1 is a schematic block diagram of a smart home control system according to a first embodiment of the present disclosure.

Referring to FIG. 1, it is a schematic block diagram of a smart home control system 100 according to a first embodiment of the present disclosure. The smart home control system 100 includes a host 11, a memory 12, at least one sensor 13 (one sensor being shown herein, but not limited to), a plurality of control switches 141 to 14N and an input device 15. The plurality of control switches 141 to 14N are, for example, electronic switches or valves to perform at least one of turning on/off home appliances, turning on/off a security system, turning on/off lamps, changing operating strength of home appliances, changing brightness of lamps and opening/closing windows and doors.

The memory 12 includes volatile memory and/or non-volatile memory, and is used to previously record a correspondence relationship between multiple family members and on/off of the plurality of control switches 141 to 14N. For example, the correspondence relationship is set in a setting phase by the family members, e.g., changing and setting using a human machine interface of the input device 15, wherein the input device 15 includes, for example, at least one of a mouse device, a keyboard, a joystick, a display screen, a microphone (e.g., speech agent), a touch device or the like. In some aspects, all or a part of the input device 15 is embedded in the host 11.

Referring to FIG. 2, it is a schematic diagram of the correspondence relationship in a smart home control system 100 according to a first embodiment of the present disclosure. The memory 12 records information (shown as state indication in FIG. 2) of whether each of the family members is at home or not. For example, if one family member is at home, a digital value (e.g., shown as 1) having at least one bit is used to indicate his/her state; whereas, if one family member is not at home, a digital value (e.g., shown as 0) having at least one bit is used to indicate his/her state, wherein whether one family member is at home or not is confirmed automatically by the host 11 according to the detection result of the sensor 13 (an example being given below). In other aspects, whether one family member is at home or not is set by using the input device 15, e.g., pressing a key, through conversation or clicking an icon on a graphical interface.

The correspondence relationship includes, for example, the relationship between in/out (or enter/leave) of a member with a control switch set and/or the relationship between a combination of staying members (or absent member) and a combination of control switches, as shown in FIG. 2. For example, when a male member enters or leaves the house, a first control switch set is turned on/off; when a female member enters or leaves the house, a second control switch set is turned on/off; when only elders and children are at home (i.e. staying members), a first combination of control switches is activated; whereas, when nobody is at home, a second combination of control switches is activated. Some family members are set not to activate any control switch, e.g., children. Each control switch set or combination of control switches includes at least one control switch.

The sensor 13 is used to acquire activity data of multiple family members, and transmit the acquired activity data to the host 11 for the entering/leaving identification, voiceprint identification and face recognition. The sensor 13 includes, for example, a CCD image sensor, a CMOS image sensor, a thermal sensor, an audio sensor and radio sensor (e.g., RFID) or other sensors capable of acquiring data to be used of ID recognition and in/out identification. For example, if the sensor 13 is an audio sensor (e.g., a microphone), the activity data is contained in the acquired voice data; if the sensor 13 is an image sensor, the activity data is contained in the acquired image frame; and if the sensor 13 is a thermal sensor, the activity data is contained in the acquired thermal image. To detect the entering and leaving of a member, the sensor 13 is preferably arranged at an entrance or at a position capable of monitoring at least the condition of the entrance, but the present disclosure is not limited thereto. If the sensor 13 is an audio sensor, it may be arranged at anyplace that can receive the member voice.

In some aspects, the sensor 13 includes an application specific integrated circuit (ASIC) or a digital signal processor (DSP) that performs the identification according to the activity data at first and then sends the identified result (e.g., indicated by at least one bit) to the host 11 for controlling the corresponding control switches.

The host 11 is selected from various fixed or movable computers that have calculating ability, e.g., a personal computer, desktop computer, notebook computer, tablet computer, security server or the like without particular limitations. The host 11 is coupled (e.g., wired or wireless) to the memory 12 and the sensor 13 to receive the activity data therefrom and access the memory 12. In some aspects, the memory 12 is embedded in the host 11.

The host 11 includes a processor, e.g., a central processing unit (CPU) or a microcontroller unit (MCU), to perform a member identification (ID) of one of the multiple family members who enters or leaves the house, and access the correspondence relationship in the memory 12 according to the member ID of staying members or the entering/leaving member among the multiple family members to accordingly control on/off of the plurality of control switches 141 to 14N thereby achieving the purpose of controlling home appliances.

For example, when the sensor 13 is an image sensor, the host 11 performs the face recognition according to the image frame to recognize a member ID of a entering or leaving member. The face recognition is performed by conventional face recognition algorithm as long as the facial features or parameters of every family member are recorded in a setting phase. The facial features or parameters of every family member are recorded in the memory 12 or on the cloud. When the image sensor is arranged at an entrance of the house, the host 11 recognizes the member ID when one family member passes the entrance and then changes setting of the state indication in the memory 12 corresponding to a passing member, e.g., from 1 to 0 or from 0 to 1, to indicate a state change of the passing member. The host 11 then controls the plurality of control switches 141 to 14N according to a state of the passing member or a combination of states of the staying members (i.e. members at home) or absent members (i.e. members not at home).

For example, when one family member leaves the house, all home appliances in the bedroom thereof are turned off and a leaving state is optionally shown on a display screen of the input device 15. For example, when only elders and children are left in the home, the window at balcony and the gas valve are turned off and the indoor camera or the thermal sensor are turned on.

For example, when the sensor 13 is an audio sensor, the host 11 performs voiceprint recognition according to the acquired voice data to recognize a member ID of an entering/leaving member and performs a natural language processing (NLP) to identify a proceeding direction thereof. For example, the host 11 is embedded with conversation function such that it is able to identify whether a family member is entering or leaving the house according to a dialogue with the family member to accordingly control the corresponding control switch set. The conversation function is implemented by the trained model and parameters integrated in the host 11, or by coupling a commercial intelligent voice device or smart speaker (e.g., used as an input device) with the host 11 without particular limitations.

In other aspects, the sensor 13 includes two or more than two sensors, e.g., including both an image sensor and an audio sensor. The host 11 recognizes a member ID according to the image frame and identifies a proceeding direction thereof using the NLP, or vice versa.

In some aspects, the host 11 is further connected to a network 18 to receive positioning signals of multiple family members via the network 18. The network 18 includes, for example, at least a wireless network or a local network. The position signals are provided, for example, by the positioning system of a mobile/wearable device 19 (e.g., a smart phone or smart bracelet, but not limited to) and sent to the host 11 via the network 18. In one aspect, the host 11 identifies a leaving (or absent) member and a staying member according to the positioning signals. In one aspect, the host 11 identifies a family member with the positioning signals thereof entering a predetermined range (e.g., going home within a short time) of the host 11 as an expected staying member, i.e., a number of staying members going to increase. The host 11 accesses the correspondence relationship in the memory 12 according to both the staying member and the expected staying member to control the plurality of control switches 141 to 14N, e.g., previously turning on or turning up the air conditioner, windows or water heater. This aspect is especially suitable to the case that there is no one at home, i.e. a number of staying members being zero.

Figure 3:
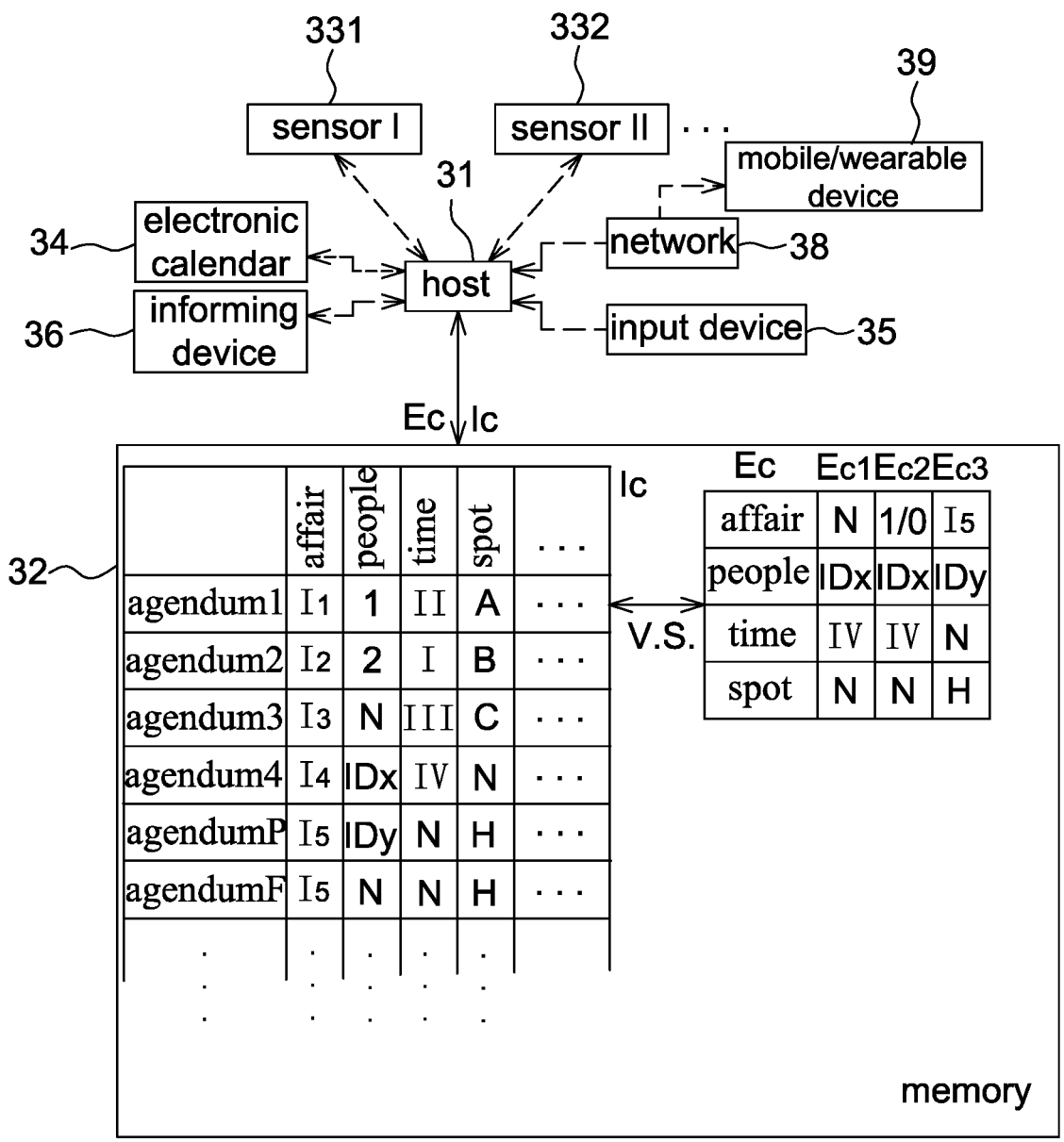
FIG. 3 is a schematic block diagram of a smart home control system according to a second embodiment of the present disclosure.

Referring to FIG. 3, it is a schematic block diagram of a smart home control system 300 according to a second embodiment of the present disclosure. The smart home control system 300 includes a host 31, a memory 32, a plurality of sensors (two sensors being shown herein, but not limited to), an electronic calendar 34, an input device 35 and an informing device 36. In some aspects, the electronic calendar 34 is edited via the input device 35 or a mobile/wearable device 39. In other aspects, the electronic calendar 34 is an individual electronic device and has its own input interface.

The memory 32 includes volatile memory and/or non-volatile memory, and is used to record multiple agenda including at least one of, for example, purchasing objects, people contact, paying bills, carrying objects, and proceeding positions, wherein the multiple agenda occur at identical or different times to be recorded by the smart home control system 300. Each of the multiple agenda is recorded by an item code having multiple bits. The item code includes, for example, at least one of a member bit, a category bit, a temporal bit and a position bit.

The member bit (shown as people in FIG. 3) is used to indicate or mark a family member (or member ID) who is suitable to execute an agendum. For example, if a digital value of the member bit is "1", it means that the associated agendum is suitable to be executed by a male member; if a digital value of the member bit is "0", it means that the associated agendum is suitable to be executed by a female or young member; and if the member bit is a null-bit (shown as N in FIG. 3), it means that the associated agendum is suitable to be executed by any family member.

In some aspects, one agendum is suitable to be executed or not executed by a family member according to more than one bit, e.g., executed by an adult and male member (e.g., the member bit having two bits, one for indicating an adult or not, and the other one for indicating a male member or not), or suitable to executed or not executed by more than one family member, e.g., not executed by an elder and a child. That is, one agendum has multiple limitations of family members indicated by the member bit.

In some aspects, one agendum is set to be executed based on a priority of family member, e.g., the member bit having another bit for indicating or defining the priority associated with one agendum. If the family member having a higher priority is not able to execute one agendum (e.g., due to the indication of other bits as mentioned below), said one agendum is automatically changed to the family member having a lower priority. In some aspects, the priority is set by more than one bits, e.g., one bit for indicating male and one bit for indicating adult; one bit for indicating female and one bit for indicating adult. In other aspects, the priority is indicated or defined by the temporal bit as below. That is, the member bit includes multiple bits respectively used to indicate different features of every family member.

The category bit (shown as affair in FIG. 3) is used to indicate or mark a type of an agendum including, for example, the purchasing objects, people contact, paying bills, carrying objects, proceeding positions (shown as $I_1$ to $I_3$ in FIG. 3, but not limited to) as mentioned above. The type of an agendum may be set and changed by family member(s) via the input device 35 or preset in the smart home control system 300.

The temporal bit (shown as time in FIG. 3) is used to indicate or mark an execution interval or priority of an agendum. For example, if a digital value of the temporal bit is "1", (show as I in FIG. 3) it means that the associated agendum is a normal level and it is not necessary to accomplish this agendum in a hurry. In this case, when a family member associated with a current event does not match this agendum (illustrated by an example below), the family member is not informed to execute this agendum. However, if a digital value of the temporal bit is "10" (show as II in FIG. 3), it means that the associated agendum is an emergency. In this case, even when a family member associated with a current event does not match this agendum, the family member is still informed to execute this agendum. For example, if one agendum is set to be executed by a male member but when the temporal bit of the one agendum is indicated as an emergency, this agendum is still informed to other family members. In some aspects, even though a current agendum is indicated as an emergency, the current agendum is never informed to a specific member, e.g., never noticing a kid or elder, but not limited thereto. That is, some agenda are always set to be executed or not executed by a specific family member.

Besides, if a digital value of the temporal bit is "11" (show as III in FIG. 3), it means that the associated agendum is preferably executed at morning; and other digital values of the temporal bit are used to indicate that the associated agendum is preferably executed in other interval of a day, e.g., in the afternoon or at night. That is, the temporal bit includes more than one bit to indicate different features, e.g., priority and suitable interval, of the agenda if required.

The position bit (shown as spot in FIG. 3) is used to indicate or mark an execution position of an agendum, e.g., convenient store, supermarket, restaurant, book store, friend's home (shown as A to C in FIG. 3, but not limited to). That is, different digital values of the position bit are used to indicate different positions of one agendum.

In some aspects, as long as the category bit of one agendum is determined, the corresponding member bit, temporal bit and spot bit are determined. In the present disclosure, one agendum is suitable to be executed by more than one family member, within more than one interval and/or at more than one position.

It is appreciated that a bit number of the item code (Ic) is determined according to the information needed to indicate.

In another aspect, the smart home control system 300 includes multiple registers to respectively indicate the item code including the member bit, the category bit, the temporal bit and the position bit. That is, the host 31 sets the item code by setting the state of the multiple registers.

The smart home control system 300 sets the item code of agenda according to detection results of the plurality of sensors 331, 332 . . . . In some aspects, the sensor is embedded in a smart home appliance, e.g., in a smart refrigerator or a smart lamp device. The smart refrigerator is integrated with multiple sensors used to detect storage amount of goods and the detected result is sent to the host 31 after the smart refrigerator is coupled to the host 31. In other aspects, the sensor is arranged as individual CCD image sensors, CMOS image sensors, thermal sensors, audio sensors, radio sensors (e.g., RFID) or the like.

The host 31 is selected from various fixed or movable computers that have calculating ability, e.g., a personal computer, desktop computer, notebook computer, tablet computer, security server or the like without particular limitations. The host 31 is coupled (wired or wireless) to the memory 32 and the plurality of sensors 331, 332 . . . to give a new item code of a new agendum detected by one of the plurality of sensors, and the new item code is recorded in the memory 32. For example, when a smart refrigerator detects that the egg is run out or when a smart lamp device detects that a lamp is burn-out, a signal is sent to the host 31. The host 31 takes this signal as a new agendum, and gives, for example, the member bit as N, the category bit as shopping (e.g., $I_1$), the temporal bit as I (e.g., normal item), and the position bit as supermarket (e.g., A) as a new item code to be recorded.

In some aspects, the host 31 further compares (in a bit-by-bit manner) the correlation or similarity of a new item code of a new agendum with the item codes of the recorded multiple agenda (i.e. the existed agenda) to confirm whether to combine or link (e.g., to be informed together) the new agendum to one of the existed agenda. For example, when the member bit, category bit, temporal bit and position bit of a new agendum are fully identical to the item code of one existed agendum or a list of existed agenda, the host 31 combines or links the new agendum to the existed agendum or the list of existed agenda to improve the operation efficiency.

In some aspects, if one bit of a new item code of a new agendum is set as "Null", the one bit of the new item code is similar or correlated to a corresponding bit of any recorded item code, i.e. null-bit having no limitation and having a lowest priority. Accordingly, if the new agendum is combined or linked to one recorded agendum that has limited item code, e.g., limited to be executed by a specific member, within a specific interval or at a specific spot, the new agendum (originally having null-bit) is then limited to be executed by the same limitation as the recorded agendum to which the new agendum is combined or linked, i.e. null-bit being changed to be the same as the recorded agendum.

In other words, the host 31 monitors the happening in the house via a plurality of sensors 331, 332 . . . and sequentially gives a code thereto to be recorded in the memory 32 as the agenda. Besides, an agendum may be known by checking the electronic calendar 34. For example, if one family member edited an appointment with someday in the electronic calendar 34, after checking the electronic calendar 34, the host 31 takes this appointment as a new agendum and gives an item code (including bits of people, affair, time and spot as shown in FIG. 3) thereof to be recorded in the memory 32. The recorded agendum is informed to the associated family member at the someday.

When recognizing a current event, the host 31 gives an event code (Ec) of the current event, and then compares the event code with the recorded multiple item codes (Ic) to determine related agenda of the current event among the existed multiple agenda. For comparing with the item codes, the current event is also preferably indicated by people, affair, time and spot, e.g., the event code includes at least one of an event member bit, an event category bit, an event temporal bit and an event position bit corresponding to the item bits. Similarly, in one aspect, the event member bit, the event category bit, the event temporal bit and the event position bit are indicated by multiple registers.

The comparing is to confirm whether the corresponding bits are identical. When digital values of every bit or register indication of the item code of one agendum are totally or partially (e.g., bit having high priority as mentioned above) identical to those of the event code, the agendum is considered as a related agendum (i.e. item code and event code matching). In the comparing procedure, the host 31 stores the generated event code into the memory 32 at first and then compares with the existed item codes, or the host 32 directly compares the generated event code with the existed item codes and the event code is then cancelled after the comparison. As mentioned above, in the comparing procedure, if one bit of the item code or the event code is indicated or given as "Null", the null-bit is similar or correlated to the corresponding bit.

In the present disclosure, the current event is an event triggered by a person, e.g., including family member leaving and family member having a phone call, but not limited thereto. As long as an event triggered by a person may be linked to deal with an existed agendum at the same time, this event is considered as a current event herein.

In one aspect, it is assumed that the sensor 331 is an image sensor. The host 31 recognizes a member ID according to image frames captured by the image sensor (e.g., face recognition mentioned above) and identifies whether the associated family member goes out or not, e.g., according to the proceeding direction of the member image. When the host 31 identifies a specific member leaving the house, an event code of a leaving event is given. For example, the event member bit is set as a digital value indicating a male member (and an ID if there are more than one male members in the family), the digital value of the event category bit is set by recognizing the dressing (e.g., wearing sportswear) of the male member, and the digital value of the event temporal bit is set according to his leaving time. If it is not able to define the event position bit, the event position bit is set as null-bit, or the proceeding position is identified using other ways (illustrated by an example below).

When the host 31 identifies that the leaving event has related agenda, the informing device 36 is used to inform the related agenda of the current event. The informing device 36 includes a mobile device, a display screen or a dialogue system. The host 31 informs, via the informing device 36, the leaving member such related agenda regarding the goods to be purchased, positions to proceed and items to be carried.

In another aspect, it is assumed that the sensor 332 is an audio sensor. The host 31 recognizes a member ID according to the voice data acquired by the audio sensor (e.g., by the voiceprint as mentioned above) and identifies whether the associated member is having a phone call (e.g., by NLP as mentioned above). After the host 31 identifies a member ID who is on the phone, an event code of a calling event is given. For example, the event member bit indicates an ID of a family member who is having the phone call, the event category bit indicates a phone call, the event temporal bit indicates a calling time zone, and the event position bit indicates at home.

In the present disclosure, when the host 31 is not able to identify a feature of any bit of the member bit, the category bit, the temporal bit or the position bit, the bit is set as null-bit. In comparison, the null-bit matches (e.g., correlated with or similar to as mentioned above) any digital value of a corresponding bit.

When identifying that the calling event has related agenda, the host 31 informs the related agenda of the current event using the informing device 36, e.g., the content to tell the person at the other side of the phone.

Similarly, the host 31 identifies and sets digital values of every bit of a current event according to the detection results of more than one sensor, e.g., performing the face recognition according to the image frame and confirming the heading position or activity according to the voice data.

In other aspects, the host 31 determines every bit of the event code of a current event according to the daily schedule. For example, one of the family members goes to the same position or has the same activity every day or someday of a week, the host 31 sets the event code of a leaving event when identifying the family member goes out at that specific time. The host 31 then actively compares the event code with the accumulated multiple item codes of multiple agenda to confirm the related agenda. The daily schedule is set by the family member via the input device 35 or actively identified according to the feedback of the mobile/wearable device 39.

In other aspects, the host 3 is used to determine the event code according to the content of the electronic calendar 34. For example, when recognizing that one family member is going out (e.g., according to the image frame or voice data), the host 31 retrieves the proceeding position and purpose by checking the electronic calendar 34 to accordingly set the digital values of every bit of the event code to be compared with the recorded item codes.

The position bits of the item code and/or the event code may also be set according to the historical paths of a family member. For example, shops, restaurants or addresses passed by when the family member goes to or comes back from the job position are used to set the position bit. That is, the position bit is not set according to a single position. For example, the smart home control system 300 is connected to a network 38 to receive positioning signals of the family members via the network 38. The positioning signals are generated, for example, by the mobile/wearable device 39 of the family members and transmitted to the host 31 via the network 38. In this way, the host 31 determines the digital values of the position bits of the item code and/or the event code according to the historical paths of the positioning signals. For example, if one family member will pass some specific positions in the way to and from the job position, the host 31 indicates the position bit of an agendum to include multiple passed positions. When detecting that the family member goes to work, the host 31 takes the agendum as a related agendum of the going to work event. It should be mentioned that although the historical paths are illustrated by the job position, the present disclosure is not limited thereto. The historical paths are determined according to any position that a family member goes frequently.

In this embodiment, after the host 31 informs a related agendum using the informing device 36, the informed agendum is not immediately removed from the list of recorded multiple agenda. When one agendum is confirmed to be accomplished by one of the plurality of sensors (e.g., new eggs being put in the case, new lamp being exchanged), by the audio sensor, by the electronic calendar 34 or by input of the input device 35, the host 31 then removes the accomplished agendum from the list of recorded multiple agenda.

The item code and/or the event code may be changed or set via a human machine interface of the input device 35, wherein the input device 35 includes, for example, at least one of a mouse device, a keyboard, a joystick, a screen, a microphone and a touch device. When the input device 35 is coupled to the host 31, the host 31 executes the corresponding control and gives the response based on the installed software and/or hardware. In some aspects, all or a part of the input device 35 is integrated in the host 31.

Figure 4:
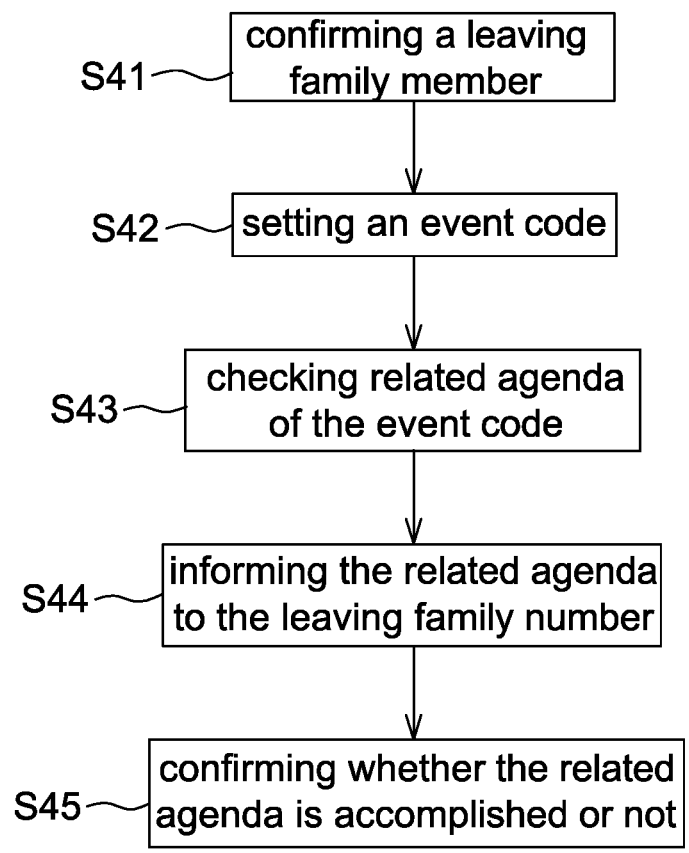
FIG. 4 is a flow chart of an operating method of a smart home control system according to a second embodiment of the present disclosure.

Referring to FIG. 4, it is a flow chart of an operating method of a smart home control system 300 according to a second embodiment of the present disclosure. The operating method includes: confirming a leaving family member (Step S41); setting an event code (Step S42); checking related agenda of the event code (Step S43); informing the related agenda to the leaving family number (Step S44); and confirming whether the related agenda is accomplished or not (Step S45). In this embodiment, the current event is illustrated by a leaving event as an example. As mentioned above, the current event may be other events triggered by a person. Referring to FIGS. 3-4 together, details of one example of this operating method are illustrated below.

Step S41: Before the occurring of a current event, it is assumed that the memory 32 has previously recorded at least one agendum. As mentioned above, the agendum is detected by the sensors 331, 332 . . . , confirmed from the electronic calendar 34, or inputted via the input device 35. The host 31 detects the current event via the sensors 331, 332 . . . , e.g., a family member going out, and the detecting method has been illustrated above and thus are not repeated. When the host 31 is triggered by the current event, the Step S42 is entered.

Step S42: The host 31 sets the event code, including changing the digital value or register states, of the current event according to the detection results of the sensors or information from other peripheral devices (e.g., electronic calendar 34 or input device 35). As mentioned above, the host 31 may or may not store the generated event code into the memory 32.

Step S43: Next, the host 31 checks whether the existed agenda have any related agendum of the event code. As mentioned above, the host 31 checks the related agenda by comparing the event code with every item code. It is appreciated that if the memory 32 does not record any agendum, the comparing is not performed.

Step S44: If the memory 32 does contain the related agendum of the event code of the current event, the host 31 uses the informing device 36 or the mobile/wearable device 39 to notify the event member to execute the related agendum. If the agenda in the memory 32 do not match (correlated or similar) the event code (e.g., more than a predetermined number of corresponding bits having different digital values), the recorded agenda are not informed to the current event member and awaiting to be executed by other family members.

Step S45: Finally, when the host 31 receives a message indicating that one agendum is accomplished, e.g., from the sensor 331, 332 . . . , electronic calendar 34, the input device 35 and/or mobile/wearable device 39, the accomplished agendum is cancelled or removed from the memory 32.

It should be mentioned that although the second embodiment is illustrated in a way that one family member is about to go out, the present disclosure is not limited thereto. In other aspects, if the memory 32 has not recorded any agendum when one family member passes the entrance to go out, the smart home control system 300 still takes the absent event as a current event, and gives an event code (Ec) of the absent event to be recorded in the memory 32 when recognizing the absent event. If a new agendum occurs (e.g., detected by one of the plurality of sensors) when the family member is still outside, the host 31 gives a new item code to the new agendum and compares the new item code with the recorded event code to determine whether the new agendum is a related agendum of the recorded absent event. If the agendum is confirmed as a related agendum, the host 31 informs the outdoor member via the network 38 to execute the new agendum. However, if the new agendum is not a related agendum, the host 31 accumulates the new agendum in the memory 32 waiting to be informed to other family members, e.g., informed when detecting a leaving event of another family member as an example in the second embodiment mentioned above. Whether the new agendum is a related agendum is identified, for example, according to the correlation or similarity between the new item code and the recorded event code as mentioned above.

In one aspect, the informed family member can refuse to execute the related agendum, e.g. using the input device 35 or the mobile/wearable device 39 to send a refuse signal. In this case, the host 31 continuously holds the agendum waiting to be informed to other family members (in the case the agendum being suitable to be executed by more than one family member). In the case that the related agendum is set to be executed only by the informed family member, the host 31 replies that the related agendum cannot be refused.

In the smart home control system of the present disclosure, the memory further stores software and/or the host is embedded with hardware or firmware used in operation of the first, second and other embodiments.

The smart home control system of the present disclosure further helps the family member to search a specific object (e.g., cellphone, keys). For example, the family member tells the smart home control system the specific object to be searched via a smart audio assistant. The host locates the specific object by the image recognition and then informs the family member through the informing device, e.g., showing on a display screen or playing by a speaker.

The smart home control system of the present disclosure further actively reminds a leaving member to bring an umbrella or regarding the weather at the time the family member is about to go out if the raining and high temperature information is obtained from the internet.

The smart home control system of the present disclosure further actively informs, via the mobile/wearable device, the family member to deal with the situation of unclosed stove fire when there is nobody at home. Furthermore, when a fire scene is monitored, the smart home control system actively contacts the local fire brigade.

The smart home control system of the present disclosure further monitors, e.g., by analyzing captured images, the food being eaten by the family member. When it is detected that any family member is about to eat allergenic food, an alarm is provided by the host via the informing device.

The smart home control system of the present disclosure further monitors, e.g., by analyzing captured images, the fragment or fluid on the floor. When the fragment or fluid are detected, a cleaning robot is automatically informed to perform the cleaning job or family members are informed via the informing device or the mobile/wearable device by the host.

The smart home control system of the present disclosure further monitors, e.g., by analyzing captured images or thermal images, the physical discomfort of family members. For example, if the fever, falling or abnormal behavior is detected, other family members are informed by the host via the informing device or the mobile/wearable device. If the unusual situation is continuously not eliminated, a medical institution is contacted.

The smart home control system of the present disclosure further performs the environment control. For example, if the low room temperature, holding tightly the bed sheet or sneeze is detected, e.g., by analyzing captured images or thermal images, the temperature setting is increased. In this case, the controlled device is coupled to the host.

Although the above embodiments are illustrated by multiple family members as an example, the present disclosure is not limited thereto. The smart home control system of the present disclosure is further adaptable to the house having a single member and the control procedure is much easier. Meanwhile, the family member adapted to trigger or activate the smart home control system may be set or changed using the input device or the mobile/wearable device.

Since both the first and second embodiments perform the corresponding function by detecting the entering and leaving of a person, they are combinable to operate together. For example, when detecting the entering and leaving of a family member, the host controls the conducting state of the control switches and prompt the related agendum. In addition, although the above embodiments are illustrated in the way that the host performs the automatic control according to the detection results, the content in the memory may also be set and changed by a family member using the mobile/wearable device via the network.

The present disclosure further provides a smart control system that reminds the family member to take medicine on time. More specifically, the agenda recorded in the memory 32 include taking medicine agenda of some family members at predetermined times (generally 2 or 3 times a day), and the current event includes a predetermined time event regarding reaching the predetermined time. This embodiment is also implemented using the smart home control system 300 shown in FIG. 3.

Referring to FIG. 3 again, each taking medicine agendum is also recorded using an item code Ic having multiple bits, e.g., a taking medicine agendum being shown as agendum 4. When one of multiple sensors 331 and 332 detects (e.g., identified by the host 31 or by a sensor itself) a taking medicine agendum, the host 31 gives a new item code Ic of the taking medicine agendum to be added in the memory 32, wherein the item code Ic is new because it is not recorded before.

In one aspect, one of the multiple sensors is an image sensor. The host 31 gives a member bit, a category bit, a temporal bit and a position bit of the new item code of the taking medicine agendum according to a QR code, a bar code, microdots or other image codes captured by the image sensor. For example, the medicine bag or receipt is printed with the QR code, bar code, microdots or other image codes that directly contain information associated with a patient name and medicine taking times, or the printed code directs a connection to the web address or cloud to download the information associated with the patient name and medicine taking times. When a family member (i.e. the patient) comes home, he/she uses the medicine bag or the receipt to record (e.g., imaging by the image sensor) a taking medicine agendum. For example, the host 31 sets the category bit of the taking medicine agendum as I4 as well as the member bit as IDx and the temporal bit as IV; herein the position bit is irrelevant and thus is set as N, but not limited to. In other aspects, the printed code contains only the medicine taking times, and the host 31 further identifies a member ID of the patient using the image sensor, audio sensor or other sources to set the member bit IDx, and sets the category bit I4 using the input device 35. More specifically, the host 31 sets every bit of an item code Ic according to identical or different devices.

In another aspect, one of the multiple sensors is a RFID sensor. The host 31 gives a member bit, a category bit, a temporal bit and a position bit of the new item code of the taking medicine agendum according to a RFID tag read by the RFID sensor, e.g., shown as agendum 4 in FIG. 3. Similarly, the RFID tag may contain only the medicine taking times, and the host 31 further sets the member bit IDx and the category bit I4 using other devices.

In another aspect, the host 31 further gives a member bit, a category bit, a temporal bit and a position bit of the new item code of the taking medicine agendum according to input of the input device 35 or content of the electronic calendar 34, e.g., shown as agendum 4 in FIG. 3.

In another aspect, the smart control system is coupled to the mobile/wearable device 39 or the network 38 (e.g., connecting to database of hospital with accessing permission). The host 31 further gives a member bit, a category bit, a temporal bit and a position bit of the new item code of the taking medicine agendum according to communication data of the network 38 or the mobile/wearable device 39, e.g., shown as agendum 4 in FIG. 3.

The method of recording (e.g., including using sensor detection or manual input) the taking medicine agendum may be performed actively by a family member or reminded by the smart control system. According to the second embodiment mentioned above, the smart home control system 300 is able to know that one family member comes back from the hospital, e.g., according to the electronic calendar 34, the GPS signal and/or the connection with hospital. Therefore, when the family member comes home, the smart home control system 300 automatically reminds, via the informing device 36 or the mobile/wearable device 39, the family member to record a new taking medicine agendum.

Furthermore, the host 31 needs to give an event code of a corresponding current event (i.e. a predetermined time event herein) to be recorded in the memory 32. In this embodiment, the event code of the predetermined time event includes an event member bit, an event category bit and an event temporal bit, wherein the event position bit may be omitted or set as null bit (N).

In one aspect, when giving the item code Ic of the taking medicine agendum, the host 31 also gives the event code (e.g., shown as Ec1 and Ec2 in FIG. 3) of the predetermined time event at the same time. For example, the host 31 correspondingly sets the event member bit as IDx to indicate a specific family member as a patient. The host 31 correspondingly sets the event temporal bit as IV to indicate medicine taking times. The event category bit may be set in two ways, described below using an example, respectively.

In another aspect, the host 31 gives every bit of the event code of the predetermined time event according to input of the input device 35 or content of the electronic calendar 34. In one aspect, the item code Ic and the event code Ec are both given and recorded in the memory 32 before the predetermined time (i.e. medicine taking times).

When the predetermined time event occurs, the host 31 compares (e.g., calculating the correlation or similarity mentioned above) the event code Ec1 or EC2 of the predetermined time event with the recorded multiple item codes Ic to accordingly prompt or inform the taking medicine agendum via the informing device 36 when a match therebetween exists. In this embodiment, said predetermined time event occurring includes, for example, a system time of the host 31 or a current time detected by one of the multiple sensors (e.g., the image sensor detecting a time of a clock) reaches the time associated with the event temporal bit IV of the event code Ec1 or Ec2.

In one aspect, as long as the system time or current time reaches the time associated with the event temporal bit IV of the event code Ec1, the host 31 directly informs the patient (or other family members also being informed) via the informing device 36 or mobile/wearable device 39. In this aspect, an event category bit of the event code Ec may be set as N to indicate the informing is performed as long as a medicine taking time is reached.

In another aspect, when the predetermined time event occurs, the host 31 further detects whether the patient has taken medicine on time. For example, when identifying a taking medicine event according to at least one of images captured by the image sensor, audio signals received by the audio sensor, a pressing signal generated by the patient pressing a notification key, a signal sent by the medicine box (e.g., including a sensor for detecting whether pills therein being taken out), the host 31 stops prompting/informing the taking medicine agendum. In this aspect, an event category bit of the event code Ec2 may set to include "1" or "0" for indicating the prompting/informing is omitted if the patient is identified to take medicine within the medicine taking time (e.g., a time interval, such as one hour); and the prompting/informing is performed when the patient fails to take medicine within the medicine taking time.

In one aspect, the host 31 informs the taking medicine agendum no matter whether the family member associated with the member bit IDx is at home or not. For example, the informing device 36 is used when he/she is at home, or the mobile/wearable device 39 is used when he/she is not at home.

This embodiment is to take the taking medicine on time as an agendum and take the medicine taking time as a current event. In the above embodiment, the host 31 arranges the medicine taking time in the event code. In the aspect that the informed member and occurrence position are irrelevant, the host 31 records the medicine taking time in a form of an alarm (similar to setting other bits, instead of the temporal bit, as Null bit). As long as the medicine taking time is reached, the host 31 informs the taking medicine agendum without comparing the event code of the predetermined time event with recorded multiple item codes.

In one aspect, one of the multiple sensors is an image sensor, which is arranged on glasses. The glasses communicates with the host 31 via a wireless network (e.g., 38). Furthermore, the category bit of the taking medicine agendum further contains information of a type and number of pills (or the taking medicine agendum including other bits to indicate the type and number), e.g., set via the input device 35 or the mobile/wearable device 39. When identifying the predetermined time event occurs, the host 31 further recognizes the pill that has been taken or not been taken according to the image captured by the image sensor (e.g., according to the color, size and shape of pills). When identifying one pill is taken repeatedly or forgotten to take (including taking a number of pills exceeding or less than a predetermined number), the host 31 further controls the informing device 36 or the mobile/wearable device 39 to generate a corresponding prompt.

For example, when one of the multiple sensors detects a taking medicine agendum, in addition to giving a new item code of the taking medicine agendum, the host 31 further confirms a pill feature to be added in the memory 32 together with the new item code.

In the aspect of using the image code, the host 31 downloads the pill feature (e.g., including color, size and shape of pills) from the network 38 according to the image code (e.g., including download address) or downloads a picture of pills associated with the taking medicine agendum to recognize the pill feature via image recognition. When a predetermined time event occurs, in addition to reminding the taking medicine agendum via the informing device 36, the host 31 further recognizes whether pills matching the pill feature of the taking medicine agendum are mistakenly taken or not according to image frames acquired by the image sensor of the system 300 in order to give corresponding warning or prompt. The mistakenly taken herein is referred to a wrong type or a wrong number of pills being taken as well as any type of and a number of pills are forgotten to be taken (also based on image recognition) within a predetermined time interval of the predetermined time.

In addition, in the aspect of using the RFID sensor, the host 31 downloads the pill feature (e.g., including color, size and shape of pills) from the network 38 according to the RFID tag (e.g., including download address) or downloads a picture of pills associated with the taking medicine agendum to recognize the pill feature via image recognition. Similarly, when a predetermined time event occurs, the host 31 further recognizes whether pills matching the pill feature of the taking medicine agendum are mistakenly taken according to image frames acquired by the image sensor of the system 300 in order to give corresponding warning or prompt.

Furthermore, it is also possible to download the pill feature via the mobile/wearable device 39 from the network 38.

The present disclosure further provides a smart control system that reminds the family member to not eat forbidden ingredients, wherein said forbidden ingredients include allergic food, religious forbidden food, personal dislike food or ingredients forbidden due to any other reasons. More specifically, the agenda recorded in the memory 32 include forbidden agenda each including a member related agendum P and a food related agendum F as shown in FIG. 3. The member related agendum P and the food related agendum F are respectively recorded, and then combined or linked as one forbidden agendum later. This embodiment is also implemented using the smart home control system 300 of FIG. 3.

Please referring to FIG. 3 again, a forbidden agendum is also recorded by an item code Ic having multiple bits. When one of multiple sensors 331 and 332 detects (e.g., identified by the host 31 or by a sensor itself) a forbidden agendum, the host 31 gives a new item code Ic to the forbidden agendum to be added to the memory 32.

In one aspect, one of the multiple sensors is an image sensor, and the host 31 gives a member bit, a category bit, a temporal bit and a position bit of the new item code of the food related agendum F and the member related agendum P according to a QR code, a bar code, microdots or other image codes captured by the image sensor.

For example, the product package or receipt is printed with the QR code, bar code, microdots or other image codes that directly contain information associated with food ingredients, or the printed code directs a connection to the web address or cloud to download the information associated with the food ingredients. When a family member comes home, he/she uses the product package or the receipt to record (e.g., imaging by the image sensor) the food related agendum F. For example, the host 31 sets the category bit of the food related agendum F as I5 as well as the member bit as N (now the ingredient not related to any family member) and the position bit as H (indicating at home); herein the temporal bit is irrelevant and thus is set as N, but not limited to.

For example, if one family member has forbidden ingredients, the family member may take a card or a display screen having the QR code, bar code, microdots or other image codes to be imaged by the image sensor. The host 31 sets the category bit of the people related agendum P as I5 as well as the member bit as IDy and the position bit as H (indicating at home); herein the temporal bit is irrelevant and thus is also set as N, but not limited to.

The host 31 then compares (e.g., calculating the correlation or similarity) the food related agendum F and the member related agendum P. As shown in FIG. 3, since the only difference between agenda F and P is at the member bit, and the member bit of the food related agendum F is set as N, the host 31 identifies that the food related agendum F and the member related agendum P have a match, and then combines the food related agendum F and the member related agendum P as a single or linked forbidden agendum that indicates the family member IDy does not eat the content of specific product package (e.g., indicated by I5), such that the monitoring is required.

In another aspect, one of the multiple sensors is a RFID sensor. The host 31 gives a member bit, a category bit, a temporal bit and a position bit of the new item code of the food related agendum F and the member related agendum P respectively according to a RFID tag read by the RFID sensor, as shown in FIG. 3. In this aspect, each family member has an individual RFID tag, and the product package has the RFID tag for being read by the RFID sensor. Similarly, when detecting a new food related agendum F, the host 31 compares the new food related agendum F with the recorded member related agendum P to confirm whether to perform the combination or linkage.

In one aspect, when the family member brings new ingredients, he/she actively records the new ingredients at a predetermined device (including detected by a sensor or input manually). In another aspect, a storage location (e.g., refrigerator or food container) has the corresponding sensor(s), and the detecting and recording are accomplished after the new ingredients are put in the storage location.

Generally, the item code of a member related agendum P is set once, unless more or less forbidden ingredients need to be recorded.

In another aspect, the host 31 further gives a member bit, a category bit, a temporal bit and a position bit of the new item code of the member related agendum P and the food related agendum F according to input of the input device or content of the electronic calendar 34, as shown in FIG. 3.

In another aspect, the host 31 further gives a member bit, a category bit, a temporal bit and a position bit of the new item code of the member related agendum P and the food related agendum F according to communication data of the network 38 or the mobile/wearable device 39, as shown in FIG. 3.

For example, the host 31 is connectable to a central control system of a food seller (e.g., including convenient stores and supermarkets) via the network 38. When the host 31 identifies a position of a family member (e.g., according to a position of the portable/wearable device 39) being in one food seller, the host 31 constructs a connection with the central control system of the food seller. When the family member accomplishes the payment (e.g., food being scanned by a cash register), the central control system transmits the information of food ingredient associated a food list bought by the family member to the host 31 for setting the food related agendum F to be compared with the member related agendum P. The memory 32 also records the image code or RFID tag associated with the bought food received via the network 38 from the food seller.

After the family member brings back the food and put in the storage location (preferably having at least one sensor therein to detect the image code or RFID tag), the host 31 needs not to download the information of food ingredient from the network 38 again but directly records the forbidden agendum formed by combining or linking the food related agendum F and the member related agendum P according to the image code and the RFID tag for being monitored by the host 31.

In the present disclosure, every bit of the member related agendum P and the food related agendum F are set from identical or different devices.

The category bit of one item code Ic is used to indicate one or more forbidden ingredients, or the item code Ic includes another bit(s) to indicate forbidden ingredients. Multiple forbidden ingredients of one family member may be indicated within a single item code Ic (e.g., using the category bit or other bits), or respectively indicated in multiple item codes Ic. For example, one family member records multiple item codes Ic associated with different forbidden ingredients, and the host 31 compares these multiple item codes Ic to combine or link as one forbidden agendum.

When recognizing an eating event, the host 31 gives an event code of the eating event. In this embodiment, the eating event is considered as a current event, and thus also includes at least one of an event member bit, an event category bit, an event temporal bit and an event position bit. For example, FIG. 3 shows that the event member bit of an eating event Ec3 is IDy, which is a member ID recognized via the image sensor, the audio sensor or other sensors. The event category bit is shown as I5, corresponding to the forbidden agendum. The event category bit is recognized according to, for example, the image captured by the image sensor, the dialogue between family members received by the audio sensor or the food being taken out from the storage location detected by a corresponding sensor. In FIG. 3, the event temporal bit is shown as N, and the event position bit is shown as H, but not limited thereto.

The eating event is also recognized, for example, according to the image captured by the image sensor and/or according to the dialogue between family members received by the audio sensor. After an eating event is recognized and the event code Ec3 thereof is given, the host 31 compares (e.g., calculating the correlation or similarity) the event code Ec3 of the eating event with recorded multiple item codes. When a match is found (e.g., between event Ec3 and agenda P+F), the host 31 informs or reminds the forbidden agendum using the informing device 36 or the mobile/wearable device 39.

As mentioned above, the member related agendum P of forbidden agenda is always stored in the memory 32. When a family member is recognized to leave the house (e.g., according to the detection of sensors by the host 31), the host 31 temporarily halts or ignores the forbidden agenda associated with the leaving family member. That is, although the host 31 identifies that the event code of a new eating event is associated with the leaving family member, because the leaving member is not possible to eat the forbidden ingredients due to the leaving, the host 31 needs not to perform the informing or prompting.

In addition, when the forbidden ingredients are used up, e.g., the storage location being empty or inputted manually by a member, the host 31 removes the corresponding forbidden agendum from the memory 32. It is appreciated that only the food related agendum F is removed but the people related agendum P is not removed. When another new food related agendum F is detected, the another new food related agendum F will be compared with the non-removed people related agendum P again.

Although the above embodiment is described by using an eating event, the present disclosure is not limited thereto. In other aspects, when the food is taken out or put in a food container or refrigerator (e.g., having the sensor therein) by a family member, the host 31 identifies whether the food being taken out or put in matches the forbidden agendum and gives a warning if it is true. In other words, the eating event mentioned above is replaced by a food event to indicate the related motion of processing food including eating, storing and taking out.

In one non-limiting aspect, one of the multiple sensors is an image sensor that is arranged on the mobile/wearable device 39, e.g., on glasses. The memory 32 of the smart control system previously records multiple forbidden agenda each being recorded by an event code Ec, which includes at least a member bit and a category bit. As shown in FIG. 3, the member bit IDy indicates a specific family member, and the category bit I5 (or indicated by another bit) indicates forbidden ingredients associated with the specific family member. When the host 31 recognizes an eating event according to the image frame captured by the image sensor, an event code of the eating event is given, e.g., Ec3 shown in FIG. 3. As mentioned above, the host 31 may recognizes the event code Ec3 using image codes or using a pre-trained AI algorithm. The host 31 may also recognizes the event code Ec3 according to the image frame captured by the image sensor in conjunction with the detection of other sensors, e.g., the sensor in the storage location. Next, the host 31 compares the event code Ec3 of the eating event with multiple item codes of multiple forbidden agenda being recorded, and sends a prompt when the event code Ec3 matches one of the multiple item codes to prevent the associated member from eating the forbidden ingredients, wherein the prompt is given using voices or images (e.g., directly shown on the glasses) without particular limitations.

Similarly, when an image sensor is arranged on the mobile/wearable device 39, the host 31 recognizes the food event according to image frames acquired by the image sensor and gives the warning using the informing device 36.

The implementation of the "match" has been illustrated above, and thus details thereof are not repeated herein.

It should be mentioned that although the above embodiments are illustrated by using family members as an example, the present disclosure is not limited thereto. When a visitor enters the house, as long as digital data of the visitor is obtainable and recorded as a temporary item code, e.g., reading from an image code of the visitor, input from the input device 35, input via the audio sensor, obtained via network 38 (e.g. connecting to cloud), obtained from mobile/wearable device of the visitor, the smart home control system 300 is also able to provide the same monitoring and informing as the family members as mentioned above.

In addition, when the visitor leaves, the host 31 removes the temporary item code from the memory 32 to reduce a number of recorded agenda.

It should be mentioned that although the above embodiments are illustrated using the home scenario as an example, the present disclosure is not limited thereto. The smart control system of the present disclosure is also adaptable to other smart places outside the home, e.g., a restaurant or hotel as long as the smart control system of these places is able to obtain the item code of forbidden agenda of a guest under the permission of the guest (e.g., obtaining access codes from wearable device or mobile device). In this way, the item code of the guest is compared with the menu codes (e.g., considered as event codes to be pre-stored in the memory 21). Accordingly, the host 31 is informed with items on the menu that cannot be eaten by the guest such that the informing or prompting is given.

In an alternative aspect, since the host 31 previously has the menu code and the guest visiting is awaited to occur, the menu codes are considered to form the item code and the forbidden agendum of the guest is considered to form the event code, opposite to the setting mentioned above.

More specifically, the item code Ic and the even code Ec in the present disclosure are set according to different applications. Generally, an item code Ic is set prior to an even code Ec, in some scenarios being set substantially at the same time. When recognizing a current event (e.g., predetermined time event or eating event mentioned above), the host 31 compares an even code associated with the current event with recorded item codes Ic to confirm whether a match is found or not.

It is appreciated that every bit shown in FIG. 3 is only intended to illustrate but not to limit the present disclosure.

As mentioned above, in a smart home it is preferably to perform different controls corresponding to different family members and automatically give a hint to a leaving member of an agendum regarding related people, affair, time, spot and object to extend the controllable range. Accordingly, the present disclosure further provides a smart home control system (e.g. FIGS. 1 and 3) and an operating method (e.g. FIG. 4) thereof that perform the indoor automatic control or remind a family member to execute agenda according to the control method and agenda stored in the memory when a host detects the entering and leaving of a family member.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A smart control system, comprising:
   a memory, configured to record multiple agenda each being recorded using an item code comprising a member bit indicating a member ID associated with an agendum, a category bit indicating a type of the agendum and a temporal bit indicating an interval of the agendum;
   at least one sensor, comprising an image sensor; and
   a host, coupled to the memory and the at least one sensor, and configured to
     give a new item code and a pill feature of a taking medicine agendum to be added in the memory when one of the at least one sensor detects the taking medicine agendum,
     give an event code, which comprises bits corresponding to item bits of the item code, of a predetermined time event to be recorded in the memory,
     compare the event code of the predetermined time event with recorded multiple item codes by calculating similarity therebetween using software embedded in the memory when the predetermined time event occurs to remind the taking medicine agendum, and
     recognize, according to an image frame captured by the image sensor, whether pills matching the pill feature of the taking medicine agendum are mistakenly taken to give corresponding warning, using an informing device, by voices or images, to warn a wrong type or a wrong number of pills being taken, one pill being taken repeatedly or not being taken.

2. The smart control system as claimed in claim 1, wherein when the predetermined time event occurs, the host is further configured to stop reminding the taking medicine agendum when the host detects a taking medicine event using one of the at least one sensor.

3. The smart control system as claimed in claim 1, wherein the host is configured to
give the member bit, the category bit and the temporal bit of the new item code of the taking medicine agendum according to a QR code, a bar code or microdots captured by the image sensor, and
download the pill feature from a network according to the QR code.

4. The smart control system as claimed in claim 1, wherein the at least one sensor further comprises a RFID sensor, and the host is configured to
give the member bit, the category bit and the temporal bit of the new item code of the taking medicine agendum according to a RFID tag read by the RFID sensor, and
download the pill feature from a network according to the RFID tag.

5. The smart control system as claimed in claim 1, further comprising an input device or an electronic calendar, wherein the host is further configured to give the member bit, the category bit and the temporal bit of the new item code of the taking medicine agendum according to input of the input device or content of the electronic calendar.

6. The smart control system as claimed in claim 1, wherein the smart control system is coupled to a network or a mobile device, and the host is further configured to give the member bit, the category bit and the temporal bit as well as the pill feature of the new item code of the taking medicine agendum according to communication data of the network or the mobile device.

7. The smart control system as claimed in claim 1, wherein when giving the new item code of the taking medicine agendum, the host also gives the event code of the predetermined time event.

8. The smart control system as claimed in claim 1, further comprising an input device or an electronic calendar, wherein the host is further configured to give the event code of the predetermined time event according to input of the input device or content of the electronic calendar.

9. The smart control system as claimed in claim 1, wherein said when the predetermined time event occurring comprises a system time of the host or a current time detected by one of the at least one sensor reach a time associated with an event temporal bit of the event code.

10. A smart control system, comprising:
a memory, configured to record multiple agenda each being recorded using an item code comprising a member bit indicating a member ID associated with an agendum, a category bit indicating a type of the agendum and a temporal bit indicating an interval of the agendum;
at least one sensor, comprising an image sensor arranged in a storage location; and
a host, coupled to the memory and the at least one sensor, and configured to
give a new item code of a forbidden agendum, recorded with an image code, to be added in the memory when one of the at least one sensor detects the forbidden agendum,
give an event code, which comprises bits corresponding to item bits of the item code, of a food event when the food event is recognized using one of the at least one sensor, and
compare the event code of the food event with recorded multiple item codes by calculating similarity therebetween using software embedded in the memory to remind the forbidden agendum in the storage location recognized according to an image frame captured by the image sensor, having a captured image code to be compared with the recorded image code, to prevent forbidden ingredients from being eaten through giving a prompt, using an informing device, by voices or images, to remind a member not to eat the forbidden ingredients.

11. The smart control system as claimed in claim 10, wherein the forbidden agendum comprises a member related agendum and a food related agendum.

12. The smart control system as claimed in claim 11, wherein the host is further configured to compare the member related agendum and the food related agendum to perform combination or linkage therebetween.

13. The smart control system as claimed in claim 11, wherein the host is configured to give the member bit, the category bit and the temporal bit of the new item code of the food related agendum and the member related agendum according to a QR code, a bar code or microdots captured by the image sensor.

14. The smart control system as claimed in claim 11, wherein the at least one sensor further comprises a RFID sensor, and the host is configured to give the member bit, the category bit and the temporal bit of the new item code of the food related agendum and the member related agendum according to a RFID tag read by the RFID sensor.

15. The smart control system as claimed in claim 11, further comprising an input device or an electronic calendar, wherein the host is further configured to give the member bit, the category bit and the temporal bit of the new item code of the member related agendum according to input of the input device or content of the electronic calendar.

16. The smart control system as claimed in claim 11, wherein the smart control system is coupled to a network or a mobile device, and the host is further configured to give the member bit, the category bit and the temporal bit of the new item code of the member related agendum according to communication data of the network or the mobile device.

17. The smart control system as claimed in claim 10, wherein when identifying a leaving member, the host is further configured to ignore the forbidden agendum associated with the leaving member.

18. The smart control system as claimed in claim 10, wherein the at least one sensor further comprise an audio sensor, and the host is configured to recognize the food event according to detection of the image sensor and the audio sensor.

19. A smart control system, comprising:
a memory, configured to record multiple forbidden agenda each being recorded using an item code comprising a member bit indicating a member ID associated with an agendum and a category bit indicating a type of the agendum, wherein the category bit indicates forbidden ingredients recorded using image codes in the memory;
an image sensor, configured to capture an image frame; and
a host, coupled to the memory and the image sensor, and configured to
give an event code, which comprises bits corresponding to item bits of the item code, of a food event when the food event is recognized according to the image frame, and
compare the event code, recognized according to the image frame captured by the image sensor, of the food event with multiple item codes of the multiple forbidden agenda by calculating similarity therebetween using software embedded in the memory, and give a prompt, using an informing device, by voices or images, to remind a member not to eat the forbidden ingredients when the event code matches one of the multiple item codes to prevent the forbidden ingredients from being eaten.

20. The smart control system as claimed in claim 19, wherein the image sensor is arranged on glasses.

* * * * *